United States Patent [19]

Cerroni

[11] Patent Number: 5,704,088
[45] Date of Patent: Jan. 6, 1998

[54] APPARATUS FOR CLEANING OF SHARP MEDICAL AND DENTAL INSTRUMENTS

[76] Inventor: Peter M. Cerroni, R.R. #2, Box 141B, Peterborough, N.H. 03458

[21] Appl. No.: 611,645

[22] Filed: Mar. 6, 1996

[51] Int. Cl.$^6$ ................................................ A47L 25/00
[52] U.S. Cl. .................. 15/160; 15/218.1; 15/220.4; 401/9; 401/10; 401/132
[58] Field of Search .............. 15/104.93, 104.94, 15/160, 218, 218.1, 220.4; 401/9, 10, 132

[56] References Cited

U.S. PATENT DOCUMENTS

| | | | |
|---|---|---|---|
| 946,370 | 1/1910 | Kelmel | 15/160 |
| 1,951,079 | 3/1934 | Zihlman | 15/220.4 |
| 2,242,134 | 5/1941 | Lynn | 15/160 X |
| 2,517,089 | 8/1950 | Dean | 15/220.4 X |
| 2,715,291 | 8/1955 | Sweigert | 15/220.4 X |
| 2,719,313 | 10/1955 | Smith | 15/220.4 X |
| 3,205,525 | 9/1965 | Birtzer | 15/220.4 |
| 3,874,332 | 4/1975 | Meinel | 401/9 X |
| 4,716,615 | 1/1988 | Whitehead et al. | 15/220.4 |
| 5,056,180 | 10/1991 | Stanton | 15/104.94 X |

FOREIGN PATENT DOCUMENTS

| | | | |
|---|---|---|---|
| 984282 | 2/1951 | France | 15/218.1 |
| 217629 | 1/1910 | Germany | 15/218.1 |
| 3118196 | 12/1982 | Germany | 401/10 |
| 93-07452 | 4/1993 | WIPO | 15/220.4 |

*Primary Examiner*—Mark Spisich
*Attorney, Agent, or Firm*—George W. Dishong

[57] ABSTRACT

The present invention is directed to an inexpensive apparatus and a method of use thereof which provides for more safe cleaning of soiled, sharp health care instruments. The instrument to be cleaned is inserted into a flexible, sealed chamber containing a means for controllably brushing and cleaning the instrument. The user compresses the apparatus with one hand while manipulating the instrument with the other hand to clean the instrument. The user is provided more protection than conventional methods and devices against being injured by the instrument and both the user and the environment are provided more protection against being contaminated by debris carried on the instrument during cleaning of the instrument.

15 Claims, 3 Drawing Sheets

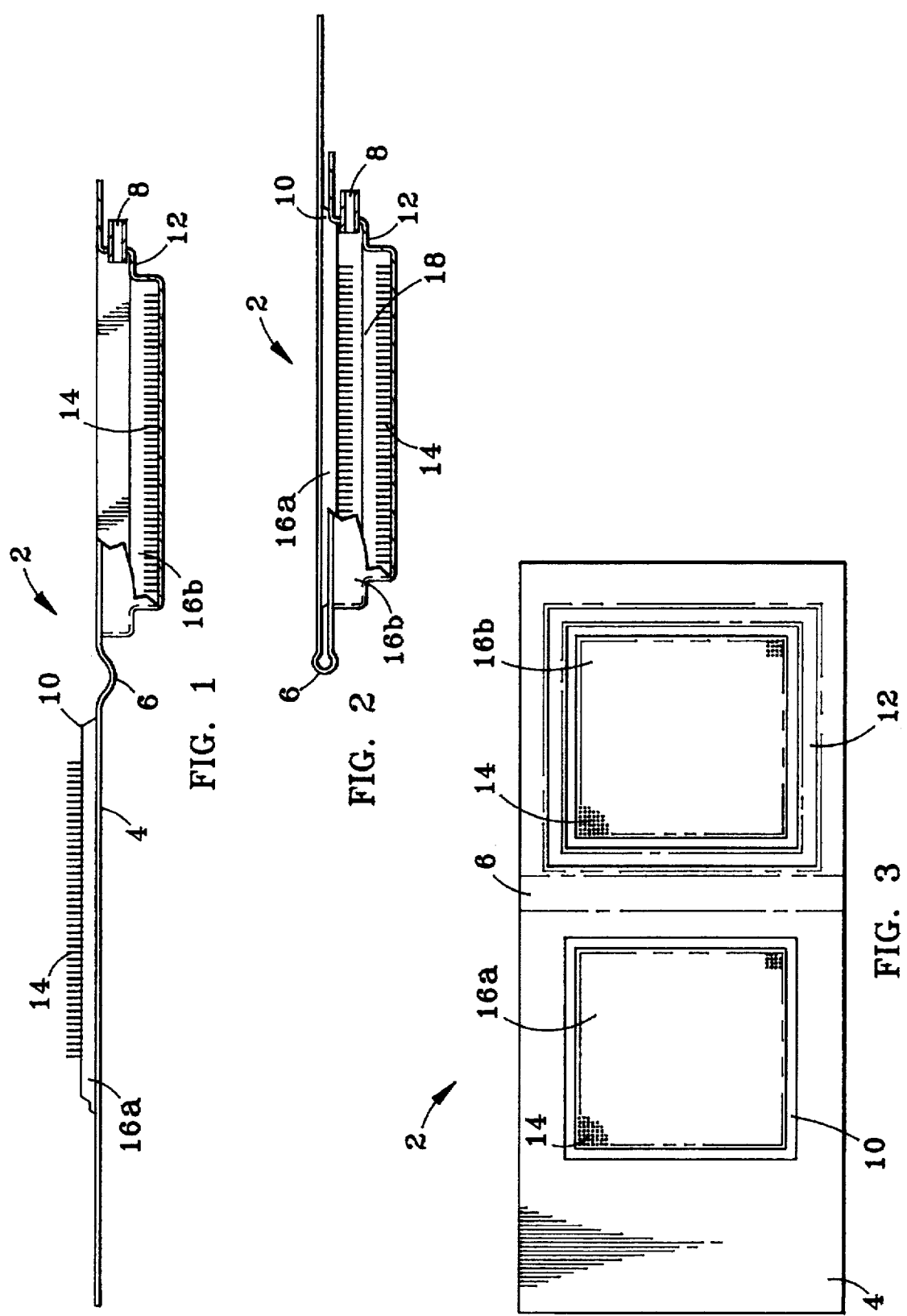

APPARATUS FOR CLEANING OF SHARP MEDICAL AND DENTAL INSTRUMENTS

BACKGROUND OF THE INVENTION

1. Field of the Invention

This invention most generally relates to a method of use and a device or apparatus for use in cleaning sharp, slender health care instruments. More particularly this invention relates to a method of use and a device or apparatus for use as an aid in debriding bioburden from dental or medical instruments during and after a medical or dental procedure, for example scaling and root planing, endodontic therapy, or tooth extraction.

Often during the course of routine medical and dental procedures reusable health care instruments are repeatedly used on the same patent. The instruments usually consist of long, slender handles often having a sharp, working tool on one or both ends. These instruments accumulate debris during the course of treatment of the patient and need to be cleaned before continuing treatment of the patient. Some of the accumulated debris might include blood, for example, which has long been recognized as a potential source of pathogenic microorganisms which may present a risk to individuals who are exposed to the organisms. In 1983 the Centers for Disease Control (CDC) published guidelines for controlling infections in hospitals. One section, entitled "Blood and Body Fluid Precautions", recommended that certain precautions be taken in handling the blood and body fluids of patients who were known infected or were suspected of being infected with blood-borne pathogens. Special precautions were recommended to be followed with such patients. The Federal Register of Dec. 6, 1991, in "Blood-Borne Pathogen Standards" under Methods of Compliance, it states in pertinent part that universal precautions shall be observed to prevent contact with blood and other potentially infectious materials under circumstances in which differentiation between body fluid types is difficult or impossible, all body fluid shall be considered potentially infectious material. Under Engineering and Work Practice Control, it notes that engineering and work practice controls shall be used to eliminate or minimize employee exposure or when occupational exposure remains after institution of these controls, personal protection equipment shall also be used such as gloves, mask etc.

Doctors and dentists are examples of the types of individuals at risk for exposure to blood-borne pathogens. During the course of treatment of a patient with a sharp-ended tool, there is the possibility of puncture of the health care professional's skin by a contaminated tool. Traditionally, for example, during the course of a routine dental check-up, the dentist probes the patient's mouth with a sharp-ended tool, removing debris and cleaning the teeth. As debris is removed, it collects on the tool, and needs to be removed before continuing treatment. A commonly used practice today involves the practitioner debriding a contaminated instrument by pressing the contaminated instrument into a folded piece of gauze held between his thumb and first finger of his or her free hand. The only barriers between the practitioner's skin and the contaminated instrument, with the use of this method, are a fairly minimal thickness of penetrable gauze and a minimal thickness of penetrable latex of a glove. Such a procedure puts the dentist/practitioner at risk of puncturing the skin with the tool and being contaminated by pathogens in the debris. Thus such a procedure does not offer adequate protection from puncture of the skin while the practitioner is cleaning the tools during treatment.

There does not appear to be any adequate, inexpensive, disposable alternative to the current and very familiar, hand-held gauze method of removing debris from instruments during patient treatment that permits the instruments to be cleaned manually using somewhat similar procedures as those procedures used with the gauze method, i.e., the ability of the practitioner to squeeze or manipulate pressure applied to the portion of the instrument being cleaned as well as to manipulate, from the handle portion of the instrument, the instrument during the manual cleaning process but at the same time provide better protection to the practitioner from punctures with contaminated instruments over that which would be available using the hand-held gauze.

2. Description of the Prior Art

Three of the most relevant United States patents were reviewed as part of the prior art. The United States Patents reviewed were U.S. Pat. Nos. 4,439,884 by Giorni, 5,308,406 by Wallock, et. al., and 5,471,706 by Wallock, et. al.

The Giorni '884 patent discloses a round, cup-like container containing an array of bristles around the inside surface of the container, all pointing towards the center of the container. The instrument is inserted through the top of the container and the bristles brush against the instrument, thereby cleaning it. The device in this patent is designed to clean the instrument in an upright position, and thereafter maintain the instrument in the container in an upright position for later use. The container is deep enough that a cleaning liquid can be put into the bottom, such that the instrument rests in a pool of cleaning liquid until used again. The container is designed for repeated use and can be clamped in place and taken apart to be cleaned.

The first Wallock patent, the '406 patent, discloses a round container similar to Giorni, with bristles covering the inner surface and extending toward the center. The device can also stand on its own and be taken apart for cleaning. It is also deep enough to hold a pool of liquid in the bottom. Additionally Wallock adds a self-sealing entrance of flexible material such that liquid does not splash out of the container during use. There is also a protective collar around the opening where the instrument is inserted in case the operator misses the entrance, such that the instrument will hit the protective collar and not puncture the user.

The second Wallock patent, the '706 patent, discloses the same container as the '406 patent with the addition of a means for withdrawing liquid from the container. Attachment to a suction device is provided to further reduce the possibility of contamination from splashing of the contaminated cleaning liquid.

SUMMARY OF THE INVENTION

The present invention provides a device and method for safely cleaning soiled health care instruments which method and apparatus permit the user thereof to manipulate the instrument within the apparatus and the manual control of cleaning pressure applied to the instrument being cleaned such that the operator is considerably less likely to be injured while treating a patient. Such a device and method are particularly useful in the medical and dental fields where sharp instruments are used repeatedly on the same patient and need to be periodically cleaned during use. The apparatus may be hand-held in the free hand (which is not performing the medical or dental procedure) of the practitioner and a contaminated instrument is placed into the device by the practitioner during and after a medical or dental procedure. This offers the practitioner a less penetrable barrier between his or her fingers and the contaminated instrument during instrument debridement.

The apparatus and method include a housing, preferably rectangularly configured, which forms a chamber therewithin, closed in all aspects except one of the walls which has an entryway which allows entry of a contaminated instrument into the interior chamber of the apparatus. The entryway may have a component which is flared away from the entryway which component acts as a guide to facilitate the entry of the contaminated instrument into the interior chamber of the apparatus. The interior surfaces of the interior chamber are smooth except for upper and lower surfaces at least one of which is or are covered with brush elements whose ends oppose each other or if only one surface has brush elements such one set of brush elements has ends inwardly directed toward the interior chamber. The brush element or elements may be separately affixed to either one or both of the upper and lower surfaces or more preferably such brush elements may be integrally formed with the housing during the fabrication of the apparatus. The brush element ends are preferably separated by airspace, i.e., the brush element ends of one set of brushes does not preferably contact the inwardly directed other brush element ends. Once a contaminated instrument is inserted through the entryway into the airspace separating the brush elements, the practitioner controllably compresses with his thumb and most likely the first finger of his free hand, the flexible, more impenetrable walls of the apparatus, engages, as a consequence of the finger pressure, the contaminated instrument and the two opposing brush elements. The practitioner then linearly and/or rotationally moves the instrument within the apparatus in a direction forwards and backwards along the axis of instrument insertion and even rotationally in order to effect cleaning of the instrument. Following as many movements as necessary to effectively debride the contaminated instrument of bioburden, finger pressure is lessened such that the instrument is no longer engaging the walls with the brush elements, thus enabling the instrument to be withdrawn from the apparatus along the original axis of insertion.

Additionally, the risk of bioburden aerosolization during insertion and removal of contaminated instruments is decreased with the present invention substantially due to the lack of contact of brush element ends with the instrument during insertion and extraction of the instrument. Other prior art cleaning devices which, by their designs, have the contaminated instruments in contact with fixed position bristles during insertion and removal of the instrument from the device cause substantial aerosolization. When there is no finger pressure on the present invention, the brush elements preferably do not touch, thus the instrument may be withdrawn without spraying contaminated material into the air during withdrawal of the instrument.

The present invention is preferably designed to be disposable after use on one patient at a single procedure to avoid cross-contamination of pathogenic organisms with other patients. Clearly however, the apparatus could also be designed using materials to form the cavity which is pliable but which could be reusable after autoclaving.

There may also be an entryway closure tethered to the apparatus for insertion into the entryway at the time of disposal of the apparatus thus to further decrease the risk of bioburden spill during disposal.

The apparatus is also preferably substantially fluid-tight such that a cleaning liquid may be optionally added to help facilitate removal of bioburden if this is desired by the practitioner.

An attachment device may also be designed onto one of the outer walls to allow the practitioner to removably attach an autoclaved mouth mirror to the apparatus. This allows the practitioner to use a mouth mirror with the apparatus attached permitting holding both the mirror and the cleaning apparatus in one hand in much the same manner as a practioner presently holds the mirror and the gauze when using the hand-held gauze method. The mouth mirror may be easily removed and autoclaved following the completion of the procedure with the patient. The attachment device could also be designed in such a manner that the apparatus could be attached to a finger of the practitioner, or to a bib or the like which is used with the patient or even to a retractable cord attached to the practitioner. Clearly there could be many means for attaching all designed to allow the practitioner to work, having the apparatus easily and conveniently accessible while working with the patient.

It is therefore an object of the invention to provide a novel apparatus and method of using such apparatus for removing debris from soiled health care instruments.

It is a further object of this invention to provide an apparatus and method of using the apparatus for removing debris from soiled health care instruments which is less penetrable then conventional gauze and latex gloves, offering the user more protection from contamination due to puncture of the skin by the soiled instrument.

It is also an object of the invention to substantially reduce contamination of the environment from cleaning of soiled health care instruments.

Yet another object of the invention is to provide a safer, less penetrable, yet inexpensive apparatus for use in cleaning soiled health care instruments during repeated use on the same patient. Such apparatus may further be disposable.

Still another object is to provide an attachment device for securing the apparatus such that it is accessible to the user, yet will not drop during the procedure.

Another object is to provide a fluid-tight apparatus such that liquid and debris do not enter the atmosphere, nor contaminate the patient or the user.

These and further objects of the present invention will become apparent to those skilled in the art to which this invention pertains after a study of the present disclosure of the invention.

BRIEF DESCRIPTION OF THE DRAWINGS

FIG. 1 is a side plan view of the instrument cleaning apparatus with the housing in the open position illustrating the hinge portion and the two opposing depressions each containing the brush element, and the opposing, matching sealing mechanism;

FIG. 2. is a side plan view of the apparatus in the closed position illustrating the chamber created by the folding of the housing and the sealing mechanism and the entrance/entryway for insertion of the instrument to be cleaned;

FIG. 3. shows a top plan view of the apparatus illustrating the trough and ridge sealing mechanism and the brush element;

DESCRIPTION OF THE PREFERRED EMBODIMENTS

Figure 4:
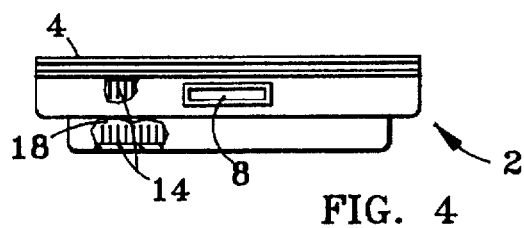
FIG. 4. shows a plan view of the apparatus from the front, looking at the entrance/entryway, the chamber and the brush element.

The instant invention is illustrated in the drawings and described as being substantially square or rectangular in shape with a relatively small depth dimension. Clearly, it is within the scope of the invention and within the objectives and advantages of the invention to provide an apparatus which has many sizes and many geometric volume configurations such as for example, capsule-shaped, ellipsoidally shaped, circular perimeter but with substantially constant thickness and the like. The material used to create the cavity or chamber need only be pliable or flexible enough to permit the practitioner to manipulate the spacing between the brushes so as to have a feel for the degree of pressure being applied to the instrument and also the orientation of the instrument within the cleaning cavity. Such a feel is considered important because of the known way in which particularly dentists and dental hygienists have been debriding instruments. The materials used to make the apparatus may be "throw-away" but need not be. Certainly the cleaning cavity, brushes and the like could be made of material which is adequately pliable to permit the feel noted above and yet be autoclavable in order to sterilize the apparatus for re-use.

It is also pointed out that the apparatus may be made in such a manner that the cavity is permanently sealed and not openable as is presently preferred. Manufacturing expediency suggests the foldable one piece, hinged and openable design as much as does the functional advantages.

Referring now in detail to the drawings, wherein similar reference numerals denote similar elements throughout the drawings, the present invention, as shown in FIG. 2, provides a hand-held apparatus 2, preferably one-piece, and foldable, for safer cleaning of soiled health care instruments by contacting them with brush element 14 inside a chamber 18 created either by folding a one-piece, flexible housing 4 or by assembly of assemblable portions, hinged or snapped together, creating thereby chamber 18. One-piece, flexible housing 4 has a hinge portion 6, as shown in FIG. 1, which allows folding of housing 4 to create chamber 18. Housing 4 also contains two opposing depressions, a first depression 16a, and a second depression 16b. Second depression 16b is preferably about twice the depth of first depression 16a. At least one of depressions 16a or 16b contains brush element 14. Preferably however, each depression, 16a and 16b contains brush element 14. Around the perimeter of depressions 16a, and 16b, are an opposing, matching ridge 10, around the perimeter of the shallower, first depression, 16a, and a matching trough 12, around the perimeter of the deeper, second depression, 16b, as shown in FIGS. 1 and 3, such that when housing 4 is folded at hinge portion 6, the two depressions, 16a and 16b form chamber 18, and ridge 10 fits securely in trough 12 to create a substantially fluid-tight seal around chamber 18.

There is an aperture or slot 8, as seen in FIG. 4, in a side wall of deeper, second depression 16b, for insertion of the instrument to be cleaned. Apparatus 2 can be either disposable after use, or reusable, by opening apparatus 2 and sterilizing it.

Housing 4 may be made from a plastic or other material which is non-absorptive and non-porous, is also resistant to heat, solvents, disinfectants, and puncture. The material is preferably also flexible/pliable and resilient such that it may be compressed by the operator to enable brush elements 14 to contact the instrument to be cleaned and to enable the operator to feel the instrument inside chamber 18 to facilitate cleaning, yet will return to its original shape after each cleaning such that the instrument may be inserted and cleaned several times during a procedure.

In the instance where brush element 14 is not integrally formed as a part of the housing bottom surfaces of depressions 16a and 16b such brush elements 14 may be permanently or at least securely attached to the bottom surface of at least one of the depressions but preferably each of depressions 16a and 16b and may be any abrasive material such as the hook portion of VELCRO® hook and loop brand of closure, ASTROTURF® brand of floor covering. Brush element 14 may also be absorbent and made of a material such as a rough sponge material, wool, or a rough cloth material such as terry cloth.

Figure 5:
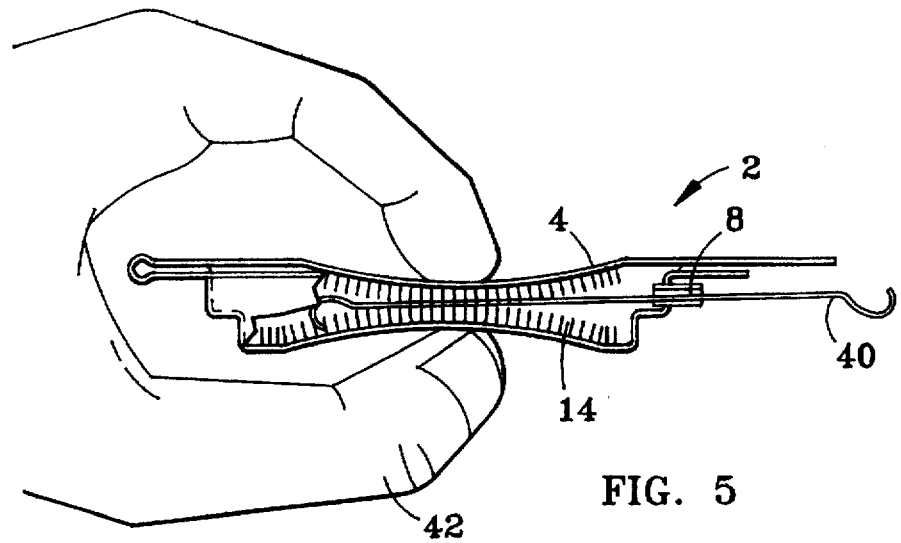
FIG. 5. is a side plan view illustrating the apparatus wherein the apparatus is compressed by the hand of the user, bringing the brush elements in contact with each other to effect cleaning of the inserted instrument.

FIG. 5. illustrates how apparatus 2 is compressed by the hand of the operator 42 to bring brush element 14 in contact with the instrument to be cleaned 40.

Figure 6:
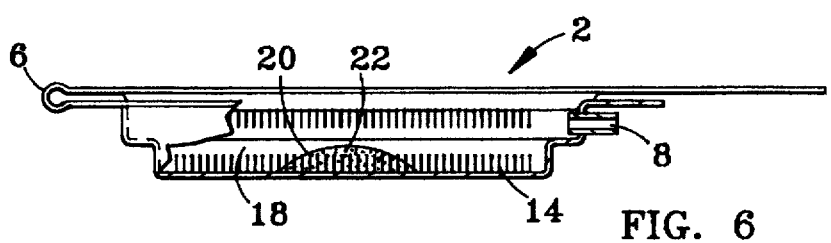
FIG. 6. is a side plan view illustrating another embodiment of the invention wherein a breakable bubble of cleaning or disinfecting solution is disposed on the surface of one of the brush elements.
Figure 7:
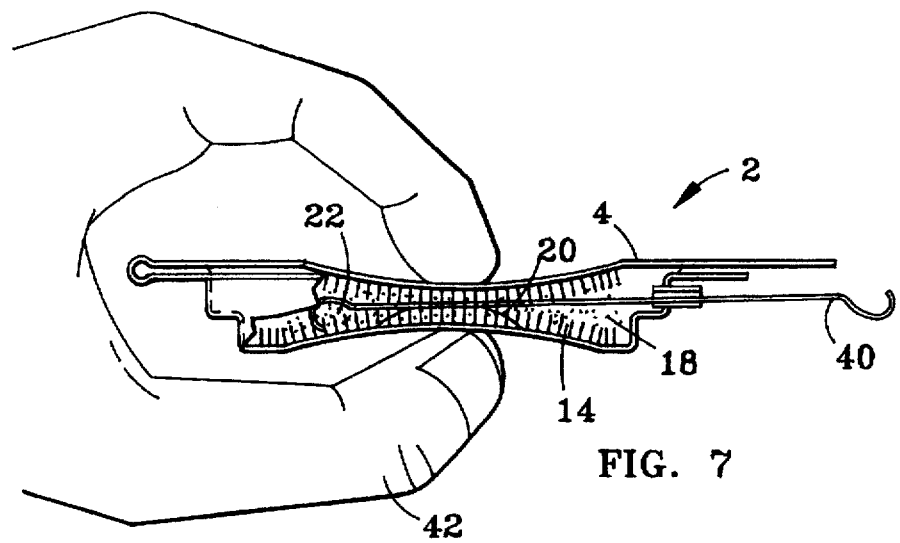
FIG. 7. is a side plan view of the apparatus in a compressed position with the bubble of cleaning or disinfecting solution broken by the compression of the apparatus and the insertion of the instrument to be cleaned.
Figure 8:
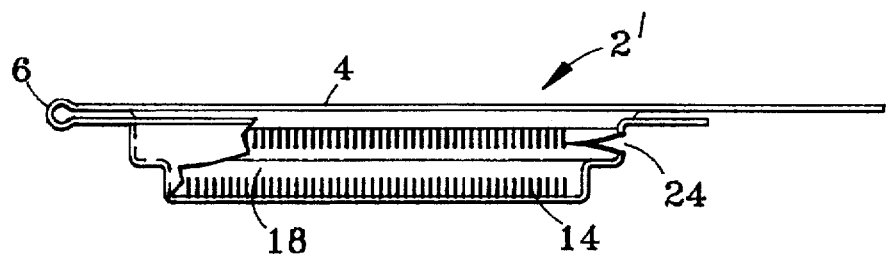
FIG. 8. shows another embodiment of the invention in side plan view wherein a flexible, substantially funnel-shaped barrier guides entrance of the instrument, such that debris remains in the chamber of the apparatus.

Another embodiment of the invention is shown in FIG. 6. which has a breakable bubble 20 of cleaning or disinfecting solution 22 disposed within chamber 18 and conveniently on a surface of one of brush elements 14 such that bubble 20 is broken and solution 22 is released upon compression of chamber 18 and insertion of the instrument 40, as illustrated in FIG. 7. The cleaning or disinfecting solution may be any conventional solution used to remove soil or to kill microorganisms.

Figure 9:
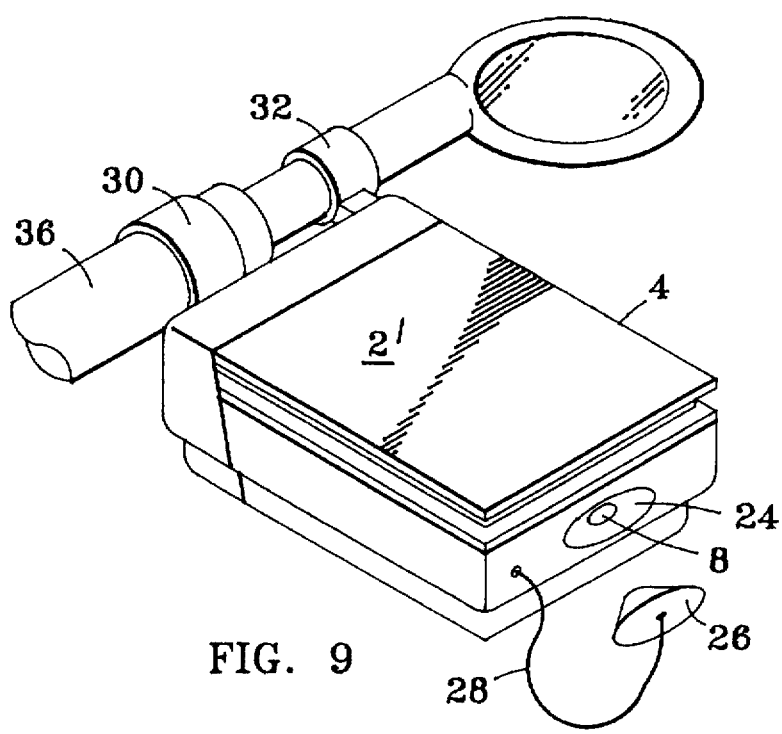
FIG. 9 shows a perspective view of the apparatus with the attachment to a mouth mirror, the substantially funnel-shaped entrance barrier and the tethered closure for disposal.

Apparatus 2 may also have a flexible, closing, substantially funnel-shaped entry barrier 24 in a side wall of depression 16b instead of entrance slot 8 such that debris removed from the instrument remains in chamber 18 so as not to contaminate the user or the environment. Flexible, closing, substantially funnel-shaped barrier 24, as shown in FIG. 9, may be of the same material as housing 4, or may be of the same material as brush element 14, or of another suitable material. Barrier 24 guides the instrument into chamber 18 (not shown in FIG. 9) to help prevent puncture of the operator by the sharp end of the instrument. Upon withdrawal of the instrument, barrier 24 wipes the instrument as it exits, and substantially closes chamber 18 behind the instrument, trapping debris in chamber 18.

Also shown in FIG. 9 is a closure 26 shaped to fit inside substantially funnel-shaped barrier 24. Closure 26 plugs barrier 24 such that chamber 18 is sealed to prevent spillage of debris upon disposal of apparatus 2 after use. Closure 26 may be made of rubber, or any appropriately flexible material, such as cork, that can be compressed slightly to seal barrier 24. Closure 26 may be tethered to apparatus 2 by means of a cord, or line 28 such that closure 26 is easily accessible to the practitioner at the end of a procedure, and will not get lost. When not in use, closure 26 may hang freely from its tether.

In another embodiment of the invention, there is provided a means for removably attaching apparatus 2 to a hand-held mouth mirror 36, as shown in FIG. 9, in order for the practitioner to use apparatus 2 without having to hold on to it as well as holding on to mirror 36 and the instrument with which he is working. The attachment may located on the outside wall of housing 4 opposite the side wall of depression 16b having barrier 24 or entrance slot 8. As shown in FIG. 9, the attachment may be a large loop 30 and a smaller loop 32 which fit around the large handle of mirror 36, and the smaller neck of mirror 36. Large loop 30 and small loop 32 may be made from a material such as Velcro® brand closure material such that they open and are then closed around mirror 36 to the desired tightness, and thereby also easily opened again and removed. Attachment loops 30 and 32 could also be made of an elastic material such that loops 30 and 32 slide over mirror 36 or other instrument or a finger into the desired position, and then slide off easily after use.

Figure 10:
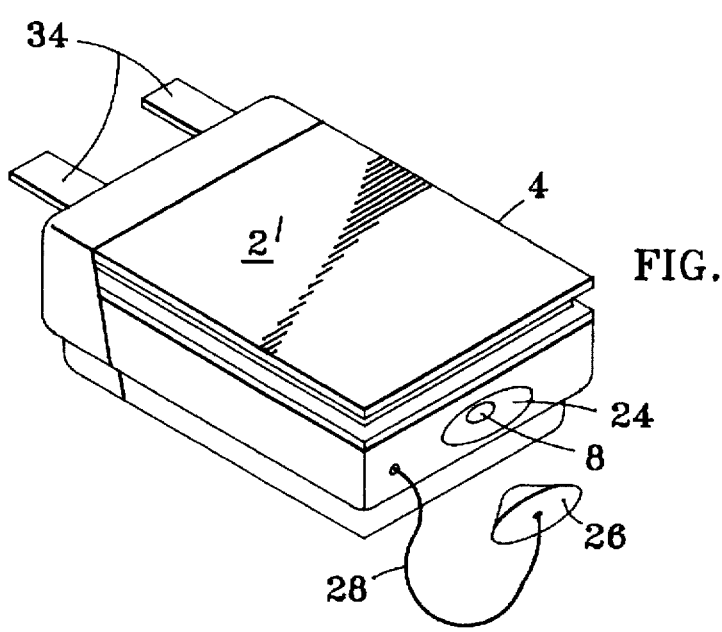
FIG. 10 shows a perspective view similar to FIG. 9 but having two small protrusions for attachment to a chord by which the apparatus may be hung, instead of loops to attach to an instrument or finger.

In yet another embodiment of the invention, apparatus 2 may be removably attached to a cord which hangs around the neck of the practitioner or may be attached to attachable to a bib on the patient or to the user. The cord my be of a reusable retractable type. As shown in FIG. 10, two small protrusions 34 may extend from the outside wall of housing 4 opposite the side wall of depression 16b having barrier 24 or entrance slot 8. A cord with two small alligator clips, or elastic loops may be attached removably to protrusions 34. In this way, apparatus 2 is easily reached and used by the practitioner, while leaving the hands more free to work on the patient.

It is thought that the present invention, the method and the apparatus for cleaning soiled health care instruments and many of its attendant advantages is understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

I claim:

1. An apparatus for cleaning sharp, slender instruments comprising:

a first housing component made from a material which is non-porous, said first housing component having a first depression therein defined by side walls and a first bottom surface;

a second housing component made from a material which is pliable, resiliently flexible and non-porous matingly and fluid-tight connectable to said first housing component, said second housing component having a second depression therein, said second depression defined by second housing side walls and a second bottom surface;

means for matingly connecting said first and second housing components at perimeters of each said first and second housing components, said first housing component and said second housing component, when matingly connected, forming thereby a substantially fluid-tight chamber having walls defined by each said first and second depressions;

brush element configured within at least one of said bottom surfaces; and a guiding entrance aperture formed in one of said side walls of said second depression whereby said instrument is guided into said chamber.

2. The apparatus according to claim 1 wherein said first housing material is pliable and resiliently flexible.

3. The apparatus according to claim 1 wherein said guiding entrance aperture is substantially funnel-shaped.

4. The apparatus according to claim 1 further comprising a hinge component connecting thereby said first and said second housing component.

5. The apparatus according to claim 1 further comprising means for substantially fluid-tight sealing said guiding entrance aperture when said instrument is withdrawn from said chamber.

6. The apparatus according to claim 3 further comprising means for substantially fluid-tight sealing said guiding entrance aperture when said instrument is withdrawn from said chamber.

7. The apparatus according to claim 4 further comprising means for substantially fluid-tight sealing said fluiding entrance aperture when said instrument is withdrawn from said chamber.

8. The apparatus according to claim 5 further comprising a breakable bubble of cleaning solution disposed within said chamber.

9. The apparatus according to claim 6 further comprising a breakable bubble of cleaning solution disposed within said chamber.

10. The apparatus according to claim 7 further comprising a breakable bubble of cleaning solution disposed within said chamber.

11. The apparatus according to claim 1 wherein each said first housing component and said second housing component is made of material selected from the group consisting of plastics, stainless steel and rubber.

12. The apparatus according to claim 1 wherein said brush element is affixed to said at least one of said bottom surfaces and wherein said brush element is made of material chosen from the group consisting of hook portion of a hook and loop fastener, artificial turf flooring material, sponge, wool and rough, absorbent cloth.

13. The apparatus according to claim 1 further comprising means for removably attaching said apparatus to a hand-held instrument.

14. The apparatus according to claim 1 wherein said apparatus is removably attachable to a cord hung around the neck of an operator.

15. The apparatus according to claim 1 wherein said apparatus has a closure shaped to fit said guiding entrance aperture permanently tethered adjacent to said guiding entrance aperture on said side wall of said second depression.

* * * * *